United States Patent [19]

Mndzhoian et al.

[11] 4,188,398
[45] Feb. 12, 1980

[54] METHOD FOR TREATING EPILEPSY

[76] Inventors: Oganes L. Mndzhoian, 2 proezd ulitsy Tumaniana, 5, kv. 6; Svetlana A. Avetisian, ulitsa Knuniantsa, 7, kv. 61; Nina E. Akopian, ulitsa Charentsa, 4, kv. 8; Dzhemma A. Gerasimian, ulitsa Moskovskaya, 8, kv. 21, all of Erevan, U.S.S.R.

[21] Appl. No.: 875,412

[22] Filed: Feb. 6, 1978

[51] Int. Cl.² ............................................. A61K 31/40
[52] U.S. Cl. ................................................. 424/274
[58] Field of Search ........................................ 424/274

[56] References Cited

PUBLICATIONS

Chem. Abst., vol. 75 (1971), 61869 k.

*Primary Examiner*—Stanley J. Friedman
*Attorney, Agent, or Firm*—Lackenbach, Lilling & Siegel

[57] ABSTRACT

The proposed anticonvulsant is intended for treating different forms of petit mal and comprises an active principle which is α-/para-isopropoxyphenyl/succinimide of the formula:

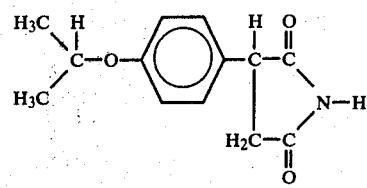

together with a pharmaceutical diluent.

1 Claim, No Drawings

METHOD FOR TREATING EPILEPSY

Field of the Invention

The present invention relates to medicine and more particularly to a novel anticonvulsant intended for treating different forms of petit mal.

SUMMARY OF THE INVENTION

The anticonvulsant of this invention is a newly developed drug of which no mention has thus far been made in the literature.

According to the invention, the proposed anticonvulsant comprises an active principle which is α-/para-isopropoxyphenyl/succinimide of the formula:

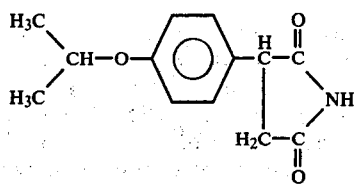

together with a pharmaceutical diluent.

The novel anticonvulsant is applicable in the treatment of different forms of petit mal and temporal forms of epilepsy, including those of vascular origin. The preparation accounts for less frequent fits and has a beneficial effect on emotional disturbances; it relieves the feeling of stress and anxiety, improves the patient's physical and mental condition, raises his or her spirits and relaxes affectivity.

DETAILED DESCRIPTION OF THE INVENTION

In the course of pharmacological studies of the novel anticonvulsant, it was compared to some well-known preparations of the succinimide group, namely, milontin, i.e., N-methyl-α-phenylsuccinimide, and zarontin, i.e., α-methyl, ethylsuccinimide. The general effect of the proposed preparation was tested on white mice, rats and rabbits.

Intraperitoneal administration of a colloidal solution of the proposed anticonvulsant to white mice weighing 20 to 25 g revealed that 200 milligrams per kilogram of weight was the least dose to produce a noticeable effect on the animals' behavior. This dose somewhat reduced the motor activity of the animals, which was greatly intensified as the dose was increased to reach 500 to 800 milligrams per kilogram of weight. Doses of more than 1,000 milligrams per kilogram of weight induced the animals to assume a lying position and to sleep.

In tests on white rats weighing 120 to 140 g, motor activity was suppressed with doses as great as 400 to 500 mg/kg. Doses of 500 to 600 mg/kg caused no conspicuous changes in the behaviour of rabbits weighing 2.5 to 3 kg.

When administered per os, the effect of the preparation on the general state of the animals was not as marked as in the case of intraperitoneal administration.

Milontin produced similar effects in much lesser doses. For example, doses of 300 to 350 mg/kg strongly suppressed spontaneous motor activity in mice, while doses of 450 to 500 mg/kg made the animals lie sidelong.

Unlike the proposed anticonvulsant and milontin, intraperitoneal injections of zarontin in doses of 500 to 600 mg/kg boosted the motor activity of the animals, making some of them stumble or run in circles. Doses of as much as 700 mg/kg also caused tremors of the hind extremities. Excitation periodically gave way to depression. At 900 mg/kg and upwards, sleep was induced.

The acute toxicity of the proposed preparation was tested on white mice weighing 19 to 20 g, by single intraperitoneal administrations of 1.5- and 10-percent colloidal solutions of the anticonvulsant in a 0.5-percent solution of carboxymethyl cellulose. The animals were observed during 48 hours. In order to establish the median lethal dose ($LD_{50}$), the experimental data was statistically processed using the Litchfield and Wilcockson techniques. Milontin and zarontin were analyzed in the same way.

The results obtained during the determination of the acute toxicity of the proposed preparation, milontin and zarontin revealed that the proposed preparation was the least toxic of all. It was more than two times less toxic than milontin and one and half times less toxic than zarontin.

The exact $LD_{50}$ values are as follows: the proposed preparation, 2,150 mg/kg; milontin, 950 mg/kg; zarontin, 1,325 mg/kg.

The mean lethal doses of the three drugs are listed below in Table 1.

Table 1

| Preparation | $LD_{50}$, mg/kg, intraperitoneal administration at P=0.05 |
|---|---|
| Preparation in accordance with invention | 2,150 (1,930 to 2,390) |
| Milontin | 950 (792 to 1,140) |
| Zarontin | 1,325 (1,200 to 1,462) |

The effects of daily administrations of the proposed anticonvulsant, carried out over prolonged periods of time, were studied on rabbits and rats.

A 2-percent colloidal solution of the proposed preparation was introduced intraperitoneally in doses of 200 mg/kg to five rabbits. This was done once a day for eight weeks. The same amounts of a colloidal solution of a carboxymethyl cellulose were administered intraperitoneally to three control rabbits.

A colloidal solution of the proposed antispasmodic was administered per os in doses of 400 mg/kg to six rats. The drug was introduced through a metal probe once a day for eight weeks.

Every day the animals' weight and body temperature were measured, and their general state was assessed. Once a week, a general blood analysis was made, the urine was analyzed for protein, blood and biliary pigments. Upon the end of the experiment, the animals were killed (the rabbits were destroyed by air embolism; the rats were decapitated). The liver, heart, kidneys, spleen, lungs and different parts of the small intestine and stomach of the freshly killed animals were taken for pathomorphological investigation.

During the entire period of observation, no changes were registered in the weight, body temperature and general state of the animals; this equally applies to the blood and urine composition. Likewise, no changes were observed in the abovementioned organs in the course of macroscopic and microscopic histochemical investigation.

The neurotoxicity levels were determined by conducting rightening, gait, stance, muscle tone and equilibrium tests. It was established that the proposed anticonvulsant and zarontin affect the neurological status if administered in doses of 720 mg/kg and 590 mg/kg, respectively; milontin produces the same effect in a much smaller dose of 340 mg/kg.

The mean neurotoxic doses are listed below in Table 2.

Table 2

| Preparation | $TD_{50}$ mg/kg at P = 0.05 |
| --- | --- |
| Preparation according to invention | 720(588 to 883) |
| Milontin | 340(278 to 416) |
| Zarontin | 590(513 to 678) |

The anticonvulsant action of the proposed preparation was tested on mice weighing 19 to 25 g and rats weighing 120 to 150 g by conducting maximum electroshock, corazol, strychnine, camphor, nicotine and arecoline tests. The results of these tests were used to compare the anticonvulsant activity of the proposed preparation with those of milontin and zarontin.

According to the corazol convulsion test, the preparation of this invention and milontin exhibit anticonvulsive effects when administered in equal doses, their $ED_{50}$ being 86 mg/kg and 87 mg/kg, respectively. It takes almost twice as much zarontin to produce the same effect ($ED_{50}=155$ mg/kg).

According to the maximum electroshock test, anticonvulsant activity was only exhibited by the proposed preparation and milontin. According to experiments on mice, the mean effective dose of the proposed preparation is 77(52.7–112.3) mg/kg, whereas that of milontin is 64(47.4–86.4) mg/kg. The difference in the activity levels of these drugs in statistically insignificant at P=0.05.

The tests involving the preparation of the present invention, milontin and zarontin revealed a certain statistical significance of the differences in their activity levels. There is a substantial difference between the activities of the proposed preparation and milontin at P=0.05.

The antistrychnine effect is the most pronounced in the proposed preparation and is at its lowest in milontin.

According to the camphor convulsions test, the differences in the activity levels of the three drugs are statistically insignificant.

The results of the experiments are listed in Table 3.

Table 3

| Preparation | $ED_{50}$ mg/kg (corazol) | $ED_{50}$ mg/kg (strychnine) | $ED_{50}$ mg/kg (Electroshock) | $ED_{50}$ mg/kg (camphor) |
| --- | --- | --- | --- | --- |
| Preparation according to invention | 86(58.1 to 127.3) | 110(80.4 to 150.9) | 77(52.7 to 112.3) | 90(57 to 142 |
| Milontin | 87(60.8 to 124.3) | 230(191 to 277) | 64(47.4 to 86.4) | 99(65.8 to 149) |
| Zarontin | 155(117.5 to 204.5) | 152(108.5 to 213) | — | 131(100 to 171.8) |

The practical value of an anticonvulsant is reflected by what is known as the protection index which is the ratio between the mean neurotoxic dose and the mean anticonvulsant dose.

The most desirable are high-index compounds with their weak neurotoxic side effects.

With its high protection index ($I=TD_{50}/ED_{50}$), the preparation of this invention compares favorably with milontin and zarontin. Comparative data on the intensity of the anticonvulsant activity of the three drugs involved in the tests is listed in Table 4.

Table 4

| Preparation 1 | Corazol 2 | Strychnine 3 | Camphor 4 | Electroshock 5 |
| --- | --- | --- | --- | --- |
| Preparation according to invention | 8.38(5.4 to 13) | 6.55(4.5 to 9.5) | 8(4.85 to 13.2) | 9.35(6.1 to 14.38) |
| Milontin | 3.91(2.59 to 5.88) | 1.47(1.12 to 1.9) | 3.44(2.17 to 5.45) | 5.3(3.71 to 7.58) |
| Zarontin | 3.8(2.8 to 5.18) | 3.88(2.7 to 5.6) | 4.5(3.32 to 6.1 | — |

The pharmacological effect of the proposed preparation was assessed by determining the protection index PI which is the ratio between the mean lethal dose $ID_{50}$ and the mean effective dose $ED_{50}$. Comparative data on the pharmacological effects of the proposed preparation, milontin and zarontin are listed in Table 5.

Table 5

| Preparation | Corazol | Strychnine | Camphor | Electroshock |
| --- | --- | --- | --- | --- |
| Preparation according to invention | 25(16.7 to 37.4) | 19.55(14.05 to 27.2) | 23.9(15 to 38.2 | 28(18.9 to to 41.4) |
| Milontin | 10.9(7.3 to 16.3) | 4.14(3.2 to 5.39) | 9.6(6.1 to 15.1) | 14.85(10.4 to 21.0) |
| Zarontin | 8.55(6.4 to 11.5) | 8.72(6.15 to 12.4) | 10.1(7.6 to 13.4) | — |

Thus the preparation in accordance with the invention is more effective than milontin and zarontin as an anticonvulsant and pharmacologic (therapeutic) agent.

The effects of the proposed preparation upon nicotine-induced convulsions and arecoline tremor were not compared to those of milontin and zarontin, keeping in mind that the latter two are antiepileptic drugs, hence, of no interest as antiparkinsonian drugs.

As regards nicotine-induced convulsions, a dose of 300 mg/kg of the proposed preparation effectively prevents convulsions and tremor; $ED_{50}$ amounts to 190(140–251) mg/kg.

Administered in a dose of 200 mg/kg to mice, the preparation markedly reduced the intensity of convulsions.

The preparation does not hinder the development of arecoline tremor, with arecoline inducing tremor of an equal intensity and duration in both control and test animals.

Corazol convulsions and maximum electroshock tests were carried out to determine the duration of the preparation's activity. Two series of experiments were made on white mice weighing 20 to 25 g. In the first series, the preparation was introduced intraperitoneally, whereas in the second series it was introduced into the stomach through a metal probe.

The anticonvulsive action of effective doses of the proposed preparation (200 mg/kg were introduced intraperitoneally, and 400 mg/kg were introduced per os) was tested every 30 minutes on separate groups of mice, each including 100 animals. The tests were continued until complete termination of the anticonvulsive effect.

According to the corazol test, the effect of the proposed preparation, when administered intraperitoneally, reaches its maximum 60 minutes after the injection. After two hours, the effect is sharply reduced and totally disappears after three hours. The situation is somewhat different in the case of peroral administration. The anticonvulsive effect of the preparation builds up gradually and reaches a maximum of 90 minutes after the injection; this level is maintained during the next four and a half hours. After six hours, the anticonvulsive activity is gradually brought down and totally disappears after about eight hours.

The maximum electroshock test produces similar results. The effect of the preparation is maintained at its peak during seven hours.

The maximum electroshock and corazol convulsion tests make it clear that the effect of the preparation lasts longer in the case of oral administration, as compared to intraperitoneal administration.

It was established that big doses of the proposed preparation had a soporific effect, which compelled the inventors to find out if the preparation acted as a sedative when administered in anticonvulsive doses. With that aim in view, the inventors studied the effects of the preparation upon the duration of pharmacologically induced sleep. Nembutal was used as a trunk narcotic, and urethane as a cortical narcotic. The experiments revealed that the preparation of the present invention and zarontin had no effect upon the duration of urethane-induced sleep, while milontin prolonged the duration of sleep more than 3 times.

A statistically significant prolongation of the hypnotic action of Nembutal was observed only in milontin. The results of the experiments are listed in Table 6.

Table 6

| Preparation | Average Duration of Urethane-Induced Sleep, Minutes, at $P = 0.05$ |
|---|---|
| Urethane, 1,000 mg/kg | $3.3 \pm 1.4$ |
| Preparation according to the invention plus urethane | $3.2 \pm 1.3$ |
| Zarontin Plus urethane | $4.7 \pm 2.1$ |
| Milontin plus urethane | $16.5 \pm 4.6$ |
| Nembutal, 40 mg/kg | $40.8 \pm 23.04$ |
| Preparation according to the invention plus Nembutal | $99 \pm 67.6$ |

| | Average Duration of Nembutal-Induced Sleep, Minutes, at $P = 0.05$ |
|---|---|
| Zarotin plus Nembutal | $76.9 \pm 28.9$ |
| Milontin plus Nembutal | $139.2 \pm 33.2$ |

The doses of the three drugs were as follows: the proposed preparation, 100 mg/kg; zarontin, 150 mg/kg; milontin, 100 mg/kg.

Investigation of other pharmacological properties of the proposed preparation revealed its limited effect upon most functions of the organism. Administered intraperitoneally or per os, it produces no effect upon the vegetative nervous system; no changes are observed in the blood pressure, breathing and neuromuscular conduction.

Thus, the basic property of the proposed preparation is that it produces an anticonvulsive effect of a central nature.

The central action of the preparation was studied electroencephalographically. The acute experiments were conducted on curarized cats and rabbits and were aimed at investigating the effects of the preparation upon the threshold magnitude and the duration of afteraction discharges of the dorsal hippocamp, intralaminar nuclei of the thalamus and the motor zone of the cortex.

It was established that in a dose of 150 to 200 mg/kg, the proposed preparation slightly raised the convulsion threshold of the hippocamp and prevented afteraction discharges of the thalamic nuclei. The preparation of this invention does not raise the stimulation threshold of the motor zone of the cortex, but considerably reduces the period of discharges in the cortex and prevents the spread of the convulsive activity to other brain structures.

The experimental data indicate that the preparation of the present invention can be recommended for treating different forms of epilepsy.

The inventors studied some specific effects resulting from repeated administration of the proposed preparation and compared them with similar effects produced by zarontin and milontin. The inventors also studied the problems of addiction to these drugs.

The method of antagonism to corazol was used to compare the $ED_{50}$ values taken during single and multiple administrations of the proposed preparation and to establish that it is devoid of habit forming properties. In the case of multiple administrations, the $ED_{50}$ value differs from that of a single administration only by a factor of 1.57. This equally applies to zarontin and milontin. The maximum electroshock test produced similar results. Teratogenic and embryotoxic tests of the proposed preparation were carried out by using A. M. Chernukh's method on 35 mongrel white female rats weighing 150 to 200 g. The preparation was introduced per os in a dose of 400 mg/kg. In all the test rats, the pregnancy developed normally.

On the twentieth day of pregnancy, all the animals were decapitated. Visual examination of the embyros and investigation of the embryos' internal organs and skeletons did not reveal any abnormalities in their growth which in no way differed from the growth of the embryos of 15 control animals.

The preparation was further studied with regard to the threonine locus of Bacillus coli at a 0.2-mole concentration; the object was subjected to treatment during 24 hours; the survival rate of the cells was between 42 and 91 percent. The preparation exhibited an extremely weak genetic action and induced no more than 17 revertants, which figure is 1.8 times greater than that of the control (spontaneous mutation). As regards the lysin locus of actinomyces, the same doses of the preparation exhibited a weak mutagenous effect and induced no more than 41 revertants, which figure is thrice as great as that of the control.

The preparation exhibited no mutagenous effect when studied on the same microorganisms with the use of the Air-Shibalsky technique.

Thus, the two testing techniques revealed no mutagenous effect of the proposed preparation upon microorganisms.

The preparation was studied clinically on 267 patients, including 72 children.

The therapeutic effectiveness of the preparation was evaluated while treating different forms of epilepsy.

The patient's age was between 4 and 56 years with the period of sickness ranging from 2 to 18 years. The different forms of the disease fell into the following categories according to clinical and encephalographic data: polymorphous fits with a deep temporal or fronto-temporal focus of epileptic activity; psychomotor fits of pseudo absentia epileptica; generalized tonico-clonic convulsive fits; true absentia epileptica with myoclonic atonic fits and cerebrovascular diseases of the central nervous system, resulting in temporal epileptic fits and polymorphous fits.

The duration of the course of treatment varied from 3 months to 3 years.

The preparation of the present invention was administered per os 3 to 6 times a day; each time a patient was given a tablet of 0.25 g so that the daily dose of the preparation was 0.75 to 1.5 g. Dynamic clinicoelectroencephalographic observation showed that the proposed preparation had been the most effective in cases of polymorphous paroxysms and fits of the temporal type, in which psychomotor and psychosensorial paroxysms alternated with pseudo absentia. In a group of 40 patients, examination of other electroencephalographic convulsive manifestations was accompanied by studying focal paroxysmal phenomena in the temporal lobes. After 10 to 14 days, fits discontinued in 18 patients (with a catamnesis covering a period of more than three months); as regards the remaining 22 patients, the frequency of fits was reduced from 3 to 4 a week to 2 to 3 a month. As regards convulsive forms of epilepsy a week therapeutic effect was only observed in cases of diffusive electroencephalographic pathology. The proposed preparation proved to be ineffective in cases of secondary generalized seizures with clinically and electroencephalographically established focal changes. According to clinical and electroencephalographic data, the preparation in accordance with the present invention is the most effective in stopping minor epileptic fits associated with anterior trunkal localization of the epileptic focus. The tests revealed no pathologic changes in the blood system; no allergic manifestations or somatic abnormalities were observed.

The negligible toxicity of the proposed preparation makes it possible to use it in ambulatory clinics for treating most diverse cases, including children. In single doses of 0.5 g, the preparation exhibits a weak and short-lived sedative effect. It is important that the preparation has a beneficial influence on emotional disturbances, which phenomenon correlates to a certain extent with a reduced frequency of fits. Besides, the preparation on improves the general mood of patients, reduces affectivity, eliminates anxieties and relieves stresses. It also improves the ambivalence of reactions and the ability for mental work; night sleep becomes deeper and longer. The preparation has a soothing effect upon aggressive, quarrelsome and importune epileptics. The patients become calm, easy to deal with, and engage in productive activities.

The preparation of this invention can completely replace other anticonvulsants employed in the course of prior treatment.

Laboratory analyses of blood and urine revealed no pathological changes.

Unlike similar preparations of the succinimide group, such as morpholep and suxilep, the proposed preparation does not result in any toxic neurological complications following uninterrupted courses of treatment over prolonged periods of time (up to eight months). There were very few cases, however, when after 3 or 4 days of treatment the patients complained of slight itching of the skin, weakness and dizziness which soon disappeared without resorting to any drug therapy.

A comparison of the proposed preparation with other similar drugs shows that the former is as effective in treating petit mal epilepsy as the most widespread preparations developed in other countries. When using the preparation in accordance with the invention, an improvement was observed in 9 patients out of 11; the figure for pyknolepsin is 12 out of 14; for suxilep, 10 out of 12; and for morpholep, 12 out of 14.

Another strong point of the proposed preparation is the absence of a potentiating effect upon convulsive paroxysms, which is not always the case with other succinimides and preparations of the oxazolidines group. A comparison between the anticonvulsive effect of the proposed preparation and that of other succinimides, such as milontin and celontin, shows that the proposed preparation is somewhat more effective in what concerns psychomotor and convulsive fits.

Discontinuation or a lower frequency of seizures was observed generally 7-8 days after the beginning of treatment with the proposed preparation at a dose of 0.25 g (the daily dose being established individually).

The use of the proposed preparation never resulted in an increased frequency of fits. Another important characteristic of the preparation is the mildness of its action. The preparation does not cause weakness or dizziness in the day time, as is often the case with the benzonal and some other drugs. Apart from preventing fits of temporal epilepsy or making such fits less frequent, the proposed preparation improves the memory of actual events, as corroborated by psychologic examination. The depressing action of the proposed preparation upon the central nervous system is not as intense as that of other antiepileptic drugs. Apparently, the proposed preparation produces an anticonvulsive effect only when administered systematically; this means that the preparation of this invention is a symptomatic drug which does not affect the metabolism of the brain and the specific functional state of the brain referred to as "the convulsive disposition of the brain".

In all cases, the use of the proposed preparation went hand in hand with treating the main disease and using hypotensive, diuretic, antisclerotic and other medicines.

Some side effects were observed. When the preparation was administered shortly before bedtime, almost all the patients complained of insomnia and disturbed sleep. However, when the last dose of the preparation was taken 3 or 4 hours before bedtime, normal sleep was soon restored. Some patients complained of nausea.

According to the invention, the proposed anticonvulsant comprises an active principle which is $\alpha$-/para-isopropoxyphenyl/succinimide and a pharmaceutical diluent.

In order to produce tablets, the pharmaceutical diluent should preferably be starch or milk sugar. The content of the active principle in a single tablet is 0.25 g. The preparation is taken internally in 0.25-gram tablets 3 to 6 times a day.

The preparation of the present invention is produced by using well known techniques. The active principle, i.e., α-/para-isopropoxyphenyl/succinimide, is prepared as follows:

α-/para-isoproxyphenyl/succinic acid brought into reaction with acetic anhydride, while it is warmed up over a boiling water bath. After 2 or 3 hours of heating, the excess acetic anhydride is removed by distillation. The remaining anhydride of α-/para-isopropoxyphenyl/succinic acid is dissolved in ethyl acetate; an ethereal solution of ammonia is added to the former solution. The precipitate is filtered, washed with ethyl acetate and ether on the filter, and dried in the air.

The dry precipitate is then dissolved in water and acidified with hydrochloric acid. The resulting precipitate, which is a mixture of two isomeric α-/para-isopropoxyphenyl/succinamic acids, is filtered, washed with water on the filter, and dried in air. This is followed by cyclization effected by heating the product to a temperature of 200° to 220° C., with simultaneous elimination of water.

Aqueous alcohol is added to the solid mass thus produced; the whole is heated to a boiling point; activated charcoal is added, and the mixture is stirred and filtered.

The cooling of the solution is accompanied by a slow precipitation of crystals of α-/para-isoproxyphenyl/succinimide. The residue is filtered and again dissolved in aqueous alcohol with heating. Upon cooling, the precipitate is filtered, washed with cooled aqueous alcohol on the filter and dried in vacuum during 6 to 8 hours.

The yield of the end product is 65 to 70 percent of the theoretical.

What is claimed is:
1. A method for treating epilepsy by administering to a patient an anticonvulsant containing as an active principle, 0.25 grams of α-/para-isopropoxyphenyl/succinimide of the formula:

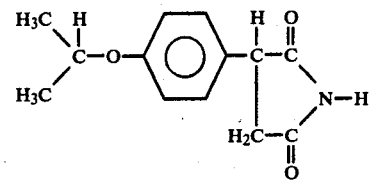

in conjunction with a pharmaceutically effective carrier.

* * * * *